United States Patent [19]

Drabek

[11] Patent Number: 4,962,126
[45] Date of Patent: Oct. 9, 1990

[54] USE OF N-(4-PHENOXY-2,6-DIISOPROPYL-PHENYL)-N'-TERTBUTYLTHIOUREA FOR CONTROLLING WHITE FLIES

[75] Inventor: Jozef Drabek, Oberwil, Switzerland

[73] Assignee: Ciba-Geigy Corporation, Ardsley, N.Y.

[21] Appl. No.: 346,361

[22] Filed: Apr. 28, 1989

Related U.S. Application Data

[63] Continuation of Ser. No. 205,594, Jun. 7, 1988, abandoned, which is a continuation of Ser. No. 882,853, Jul. 7, 1986, abandoned.

[30] Foreign Application Priority Data

Jul. 12, 1985 [CH] Switzerland ............... 3036/85
May 20, 1986 [CH] Switzerland ............... 2019/86

[51] Int. Cl.$^5$ ............................... A01N 47/28
[52] U.S. Cl. ....................................... 514/587
[58] Field of Search ............................. 514/587

[56] References Cited

U.S. PATENT DOCUMENTS

| | | | |
|---|---|---|---|
| 4,328,247 | 5/1982 | Drabek et al. | 424/326 |
| 4,404,225 | 9/1983 | Boger et al. | 424/322 |
| 4,734,433 | 3/1988 | Drabek et al. | 514/508 |

FOREIGN PATENT DOCUMENTS

1571970 7/1980 United Kingdom .
2060626 of 1981 United Kingdom .

*Primary Examiner*—Allen J. Robinson
*Attorney, Agent, or Firm*—Kevin T. Mansfield

[57] ABSTRACT

The invention relates to the use of N-(4-phenoxy-2,6-diisopropylphenyl)-N'-tert-butylthiourea for controlling insects of the family Aleyrodidae (white flies), in particular nymphs and adults of resistant *Bemisia tabaci* strains, in crops of cotton and vegetables.

6 Claims, No Drawings

USE OF N-(4-PHENOXY-2,6-DIISOPROPYLPHENYL)-N'-TERTBUTYLTHIOUREA FOR CONTROLLING WHITE FLIES

This application is a continuation of Ser. No. 07/205,594, filed June 7, 1988, now abandoned; which is a continuation of Ser. No. 06/882,853, filed July 7, 1986, now abandoned.

The present invention relates to the use of N-(4-phenoxy-2,6-diisopropylphenyl)-N'-tert-butylthiourea for controlling insects of the family Aleyrodidae (white flies).

White flies come into the category of important pests in crops of cotton and vegetables, with both outdoor and greenhouse vegetables being greatly affected. Various species of these pests have developed resistance to the compounds hitherto employed for controlling them, e.g. organophosphorus compounds and pyrethroids.

Surprisingly, it has now been found that with the compound of the formula

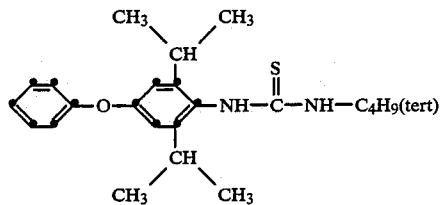

known from German Offenlegungsschrift No. 3 034 905, not only sensitive, but also resistant Aleyrodidae species can be successfully controlled. The family of Aleyrodidae comprises, inter alia, the genus Trialeurodes, e.g. the species *Trialeurodes brassicae, Trialeurodes vaporariorum* or *Trialeurodes vittata,* and the genus Bemisia, e.g. *Bemisia giffardi, Bemisia inconspicua* or, in particular, *Bemisia tabaci.* Mention is to be made of the fact that all development stages can be brought under control. Particularly advantageous results are achieved against nymphs and adults of sensitive and, in particular, resistant strains.

The compound of formula I to be used in accordance with the present invention can be prepared in known manner by reacting the isothiocyanate of the formula

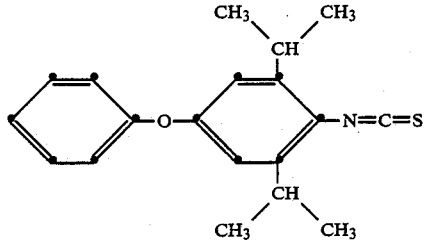

with tert-butylamine.

The process is carried out in vacuo or under normal pressure at a temperature in the range from 0° to 100° C., preferably from 20° to 50° C., and optionally in a solvent or diluent.

Examples of suitable solvents or diluents are ethers and ethereal compounds such as diethyl ether, diisopropyl ether, dioxane, 1,2-dimethoxyethane and tetrahydrofuran; amides such as N,N-dialkylated carboxamides; aliphatic, aromatic and halogenated hydrocarbons, in particular benzene, toluene, xylenes, chloroform and chlorobenzene; nitriles such as acetonitrile; dimethyl sulfoxide; and ketones such as acetone and methyl ethyl ketone.

The compound of formula II is known and can be prepared by known methods.

The compound of formula I is used in unmodified form, or preferably together with the adjuvants conventionally employed in the art of formulation, and is therefore formulated in known manner e.g. to emulsifiable concentrates, directly sprayable or dilutable solutions, dilute emulsions, wettable powders, soluble powders, dusts, granulates, and also encapsulations in e.g. polymer substances. The methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and or grinding the active ingredient with extenders, e.g. solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ethyl acetate, propyl myristate or propyl palmitate, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; silicone oils or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, and phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, New Jersey, 1982, and Dr. Helmut Stache: "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I, 1 to 99.9% of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients for obtaining special effects.

EXAMPLE 1:

Preparation of N-(4-phenoxy-2,6-diisopropylphenyl)-N'-tert-butylthiourea 19.2 g of N-2,6-diisopropyl-4-phenoxyphenyl isothiocyanate are diluted with 10 ml of toluene, and 13.7 g of tert-butylamine are then added. The reaction mixture is subsequently stirred for 12 hours at 20°–25° C. The mixture is then concentrated by evaporation and recrystallised repeatedly from hexane, affording the compound of the formula.

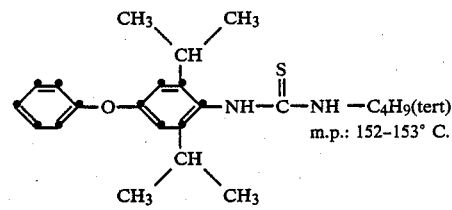

m.p.: 152–153° C.

EXAMPLE 2:

Formulation Examples for the active ingredient according to Preparatory Example 1 (throughout, percentages are by weight)

| 2.1. Emulsifiable concentrates | (a) | (b) | (c) | (d) |
|---|---|---|---|---|
| compound according to Preparatory Example 1 | 10% | 25% | 40% | 50% |
| calcium dodecylbenzenesulfonate | — | 5% | 8% | 6% |
| castor oil polyethylene glycol ether (36 moles of ethylene oxide) | — | 5% | — | — |
| tributylphenol polyethylene glycol ether (30 moles of ethylene oxide) | — | — | 12% | 4% |
| castor oil thioxilate | 25% | — | — | — |
| cyclohexanone | — | — | 15% | 20% |
| butanol | 15% | — | — | — |
| xylene mixture | — | 65% | 25% | 20% |
| ethyl acetate | 50% | — | — | — |

Emulsions of any required concentration can be produced from such concentrates by dilution with water.

| 2.2. Solutions | (a) | (b) |
|---|---|---|
| compound according to Preparatory Example 1 | 10% | 5% |
| ethylene glycol monomethyl ether | — | — |
| polyethylene glycol (mol. wt. 400) | 70% | — |
| N-methyl-2-pyrrolidone | 20% | — |
| expoxidised coconut oil | — | 1% |
| petroleum distillate (boiling range 160–190°) | — | 94% |

These solutions are suitable for application in the form of microdrops.

| 2.3. Granulates | (a) | (b) |
|---|---|---|
| compound according to Preparatory Example 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | (a) | (b) | (c) | (d) |
|---|---|---|---|---|
| compound according to Preparatory Example 1 | 2% | 5% | 5% | 8% |
| highly dispersed silicic acid | 1% | 5% | — | — |
| talcum | 97% | — | 95% | — |
| kaolin | — | 90% | — | 92% |

Ready for use dusts are obtained by intimately mixing the carriers with the active ingredient.

-continued

| 2.5. Wettable powders | (a) | (b) | (c) |
|---|---|---|---|
| compound according to Preparatory Example 1 | 20% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 67% | 27% | — |

The active ingredient is thoroughly mixed with the adjuvants and the mixture is thoroughly ground in a suitable mill, affording wettable powders which can be diluted with water to give suspensions of the desired concentration.

| 2.6. Extruder granulate | |
|---|---|
| compound according to Preparatory Example 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.7. Coated granulate | |
|---|---|
| compound according to Preparatory Example 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.8. Suspension concentrate | |
|---|---|
| compound according to Preparatory Example 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3:

Biological Test (a) Action of various insecticides compared with the compound of formula I against sensitive and resistant adults of *Bemisia tabaci*

Cotton leaves are immersed in a solution of the test substance (active ingredient concentration of 0.1 to 4100 ppm). 20 to 50 sensitive and 20 to 50 resistant adults of *Bemisia tabaci* are placed on the treated leaves in covered petri dishes.

Two tests are carried out with each test substance at each of its given concentrations.

A mortality count is made after 24 hours. The dosis-mortality line is then calculated from the percentage mortality at the individual concentrations in accordance with the Probit analysis method and the LC$_{55}$ values are determined from these lines (q.v. L. BANKI, Bioassay of Pesticides in the Laboratory, 1978).

The resultant data are summarised in the following Table:

| | LC$_{50}$ values in ppm | |
|---|---|---|
| Substance | Sensitive strain of *Bemisia tabaci* | Resistant strain (Sudan) of *Bemisia tabaci* |
| compound of formula I | 11.6 | 12.3 |
| monocrotophos | 6.5 | 1327 |
| dicrotophos | 12.8 | 1202 |
| dimethoate | 12.2 | 4029 |
| thiodicarb | 4.5 | >4000 |
| methamidophos | 5.8 | >4000 |
| fenvalerate | 1.8 | 56 |
| deltamethrin | 0.2 | 75 |
| cypermethrin | 2.9 | 140 |

(b) Action of endosulfan compared with the compound of formula I against nymphs of resistant *Bemisi tabaci*

A concentration series of 500, 250, 125, 60, 30, 15, 7.5 and 3.75 ppm of the compound of formula I and of endosulfan are prepared. 3 cotton plants in the cotyledon stage are placed in each of a number of pots. Two pots are necessary for each test substance at each of its given concentrations. Oviposition takes place within 3 days. The adults are removed from the plants by suction. After 10 days the nymphs are in the 2nd shedding stage and the plants are then sprayed to drip point. Evaluation is made after 7 to 10 days by determining the mortality under a stereoscopic microscope. At this moment the nymphs on the untreated controls are in the red eye stage.

The following Table shows the percentage mortality rate for each concentration.

| | Mortality in % | |
|---|---|---|
| Concentration in ppm | Comp. of formula I | Endosulfan |
| 3.75 | 100 | 0 |
| 7.5 | 100 | 0 |
| 15 | 100 | 0 |
| 30 | 100 | 0 |
| 60 | 100 | 0 |
| 125 | 100 | 42 |
| 250 | 100 | 51 |
| 500 | 100 | 86 |

What is claimed is:

1. A method of controlling insects of the family Aleyrodidae which comprises applying to nymphs and adults of said insects or their infected loci, an insecticidally effective amount of the compound

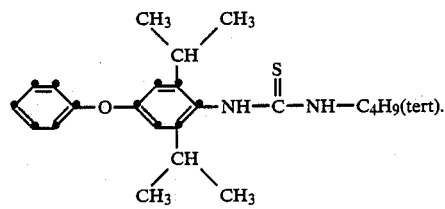

2. A method of use according to claim 1 for controlling sensitive and resistant Aleyrodidae species in crops of cotton and vegetables.
3. A method of use according to claim 1 for controlling insects of the genus Bemisia.
4. A method of use according to claim 3 for controlling *Bemisia tabaci*.
5. A method of use according to claim 4 for controlling adults of resistant *Bemisia tabaci* strains.
6. A method of use according to claim 1 for controlling insects of the genus Trialeurodes.